United States Patent [19]

Meiller et al.

[11] 4,100,149

[45] Jul. 11, 1978

[54] METHOD OF SEPARATING PROTEINS BY ION EXCHANGE

[75] Inventors: François Meiller, Palaiseau; Bernard Mirabel, Fresnes, both of France

[73] Assignee: Rhone-Poulenc Industries, Paris, France

[21] Appl. No.: 714,308

[22] Filed: Aug. 16, 1976

[30] Foreign Application Priority Data

Aug. 28, 1975 [FR] France ............................. 75 26530
Jul. 28, 1976 [FR] France ............................. 76 22985

[51] Int. Cl.² .......................... A23J 1/20; A23J 1/16; A23J 1/08; A23J 1/06
[52] U.S. Cl. .............................. 260/112 R; 526/46; 526/49; 526/194; 526/279; 528/418; 526/31; 526/317; 260/112 B; 260/122; 428/407
[58] Field of Search ............... 260/112 R, 112 B, 122, 260/2.1 R

[56] References Cited

U.S. PATENT DOCUMENTS

| 3,234,199 | 2/1966 | Reid ................................ 260/112 R |
| 3,557,082 | 1/1971 | Bridgeford .................. 260/112 R X |
| 3,969,261 | 7/1976 | Meiller ........................ 260/2.1 R X |
| 3,969,337 | 7/1976 | Lauer et al. .................... 260/112 R |
| 3,989,649 | 11/1976 | Kaiho et al. ..................... 260/2.1 R |

*Primary Examiner*—Walter C. Danison
*Attorney, Agent, or Firm*—McDougall, Hersh & Scott

[57] ABSTRACT

A method of separating proteins by ion exchange comprising putting a solution of proteins into contact with an ion exchange resin consisting of a porous inorganic carrier coated with a cross-linked polymer containing or carrying anion exchanging groups — tertiary amines or salts of quaternary ammonium — or cation exchanging groups and application of the process to the food, pharmaceutical and veterinary field.

10 Claims, No Drawings

METHOD OF SEPARATING PROTEINS BY ION EXCHANGE

The invention relates to a method of separating proteins by ion exchange.

It is known to separate proteins by ion exchange, using cellulose or dextran, having fixed thereon either tertiary amines, quaternary ammonium, or acid functions. However, these ion exchangers have no mechanical properties and consequently cannot be used in a column; their volume undergoes changes with the ionic forces and the pH of the medium of use. Moreover they are biodegradable and cannot be sterilized.

It is an object of this invention to provide ion exchange resins which do not have these drawbacks; have good mechanical properties, are not affected by the ionic force or pH of the medium of use, are not biodegradable and can be sterilized. In addition, they make it possible to obtain very pure proteins.

The protein-separating method according to the invention comprises putting a protein solution into contact with an ion exchange resin and is characterized in that the exchanger consists of a porous inorganic carrier having a particle size from 4 μm to 5 mm, a specific surface area of approximately 5 to 150 m²/g, a pore diameter of 500 to 2500 Å and a pore volume of 0.4 to 2 ml/g, that the carrier be coated with less than 15 mg/m² of a film of cross-linked polymer, containing or carrying either anion-exchange groups, represented by tertiary amines or quaternary ammonium salts, or cation-exchange groups, represented by acid functions, and that the exchanger has an exchange capacity of less than 2 meq/g.

The porous inorganic carriers used are metallic oxides such as titanium oxide, aluminas and more particularly silicas. These carriers have average pore diameters of 500 to 2500 Å and preferably from 600 to 1500 Å, a specific surface area of 5 to 150 m²/g and preferably from 20 to 50 m²/g, and a particle size of 4 μm to 5 mm, according to the application envisaged. Thus the finest particles are used for analysis and the coarsest for preparing substances.

The functional groups, tertiary amines or quaternary ammonium salts are represented by general formulae

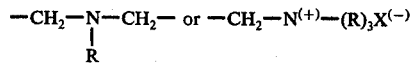

wherein R, which may be identical or different, represents an alkyl or hydroxyalkyl group with 1 to 4 carbon atoms and X represents an inorganic or organic anion, such as a chloride, sulphate, nitrate, phosphate or citrate.

The acid functional groups are represented by carboxylic, sulphonic or phosphonic groups having the general formulae —COOH, —SO₃H, —PO (OH)₂.

These functional groups either form part of the chain of the cross-linked polymer or are fixed to the cross-linked polymer which covers the whole surface of the carrier.

The cross-linked polymers, which cover the surface of the inorganic carrier, are products which are known per se and obtained by any conventional methods of polymerization. They are prepared from monomers which can be cross-linked either alone or with another monomer, often in the presence of a catalyst. The monomers include: epoxy compounds which can be cross-linked with polyamines as catalysts; the formaldehyde, which can be cross-linked by polycondensation without a catalyst with urea, melamine, polyamines, phenols; and vinyl monomers: vinylpyridine, styrene and derivatives, vinylbenzoic acid or acrylic and/or methacrylic acids, which can be cross-linked with polyfunctional monomers: mono- or polyalkylene-glycol diacrylate or dimethylacrylate, divinylbenzene, vinyltrialkoxysilane, vinyltrihalogenosilane, bis methyleneacrylamide, in the presence of an initiator to liberate free radicals like organic peroxides and azonitriles, or UV radiations.

To obtain the coating of cross-linked polymer on the inorganic carrier, the carrier is impregnated with a solution of the monomer or monomers and possibly the catalyst in a solvent, thus enabling the monomers to be distributed evenly over the entire surface of the inorganic carrier. The solvent is then evaporated and the monomers cross-linked by known methods. The solvent used may be any substances which will dissolve the monomers and catalyst, having a boiling point preferably as low as possible in order to encourage subsequent evaporation. Some examples of such solvents are methylene chloride, ethyl ether, benzene, acetone and ethyl acetate.

A method particularly adapted to the preparation of an cationic exchanger, by coating carriers with epoxy compounds, has been described in the copending application Ser. No. 607,094, filed Aug. 25, 1975, in the name of Meiller, and entitled "Modified Mineral Supports."

In cases where the polymer cross-linked to the surface of the inorganic carrier does not have any functional groups in the chain, as defined above, it has to be modified; this applies particularly to cross-linked polymers based on styrene and derivatives, and polymers of formaldehyde with urea, melamine, polyamines, or phenols.

In the case of styrene or phenol-formaldehyde polymers, such modification comprises fixing either carboxylic, sulphonic, or phosphonic groups on the polymer by any known method or by fixing chloromethyl groups on the polymer and then reacting them with a secondary or tertiary amine by any known process.

When fixing chloromethyl groups on the polymer, it is advantageous, in the case of styrene polymers, to disperse the inorganic carrier coated with polymer hot in chloromethyl ether in the presence of a Lewis acid. In the case of a phenol-formaldehyde resin, on the other hand, the inorganic carrier coated with polymer may, e.g., be dispersed in epichlorohydrin and reacted at elevated temperature.

In the case of polymers of formaldehyde with urea, melamine, or polyamines, the modification comprises converting the primary amines present in the chain into tertiary amines or salts of quaternary ammonium by any conventional method, e.g., by reaction with an alkyl sulphate or halide.

In the operation of coating the inorganic carrier, the quantity of monomer(s) used must be such that the quantity of cross-linked polymer with functional groups, distributed over the surface of the inorganic carrier, is less than 15 and preferably from 1 to 8 mg/m².

The resultant inorganic carriers, coated with cross-linked polymers having functional groups, have an exchange capacity below 2 meq/g and preferably from 0.3 to 1.2 meq/g.

The method of the invention applies to all proteins soluble in an aqueous medium, whatever their isoelectric point.

The following are some examples of such proteins, which include polypeptides and enzymes; albumin, lactalbumins, egg albumin, serum albumin, haemoglobin, α, β and γ globulins, lactoglobulins, fibrinogen, urease, trypsin, lysoxyme, pepsin, proteases, and cytochrome.

The method of the invention enables proteins to be separated very easily from their solutions, such as milk serum, beer, blood, extracts from organs and from any industrial effluent; waste water from slaughter houses, the food industry or potato starch works. It thus provides a means of purifying such effluents and hence a means of avoiding pollution.

Separation is obtained by putting the solution to be treated into contact with the ion exchange resin at a temperature, ionic force and pH compatible with the protein or proteins, the resin being selected according to the separating conditions. Either the required protein, or the other protein or proteins contained in the solution, or all the proteins in the solution are then fixed on the ion exchange resin.

Separation may equally be obtained under the same conditions by putting the solution to be treated into contact with one or more anion-exchange and/or cation-exchange resin in succession. The proteins in the solution are then fixed selectively on each resin.

In cases where the required protein is fixed on a resin from a protein solution, it is then separated by elution with a solution that has a pH and/or an ionic force different from those of the fixing solution yet compatible with the protein. This leads not only to separation of the protein from the solution but also to its purification and concentration. In this way, albumin, pepsin and proteins from milk serum may, e.g., be separated and concentrated with a cationic resin and lysozyme with an anionic resin.

In cases where the required protein remains in the protein solution treated according to the invention and the other proteins in the mixture are fixed, the required protein is separated from the other proteins and thus purified. Elution of the proteins fixed leads to their selective or nonselective separation and concentration. This applies inter alia to γ-globulin with a cationic resin.

In cases where a plurality of required proteins are fixed simultaneously on a resin, elution at a pH and/or an ionic force different from those of the fixing solution causes the proteins to be separated from the solution and concentrated. Elution by solutions with an increasing pH and/or ionic force leads not only to selective separation but also to purification and concentration. This is particularly the case with human serum.

In cases where the proteins have to be eliminated, they are fixed on a resin from their solution. This gives solutions which are deproteinized, that is to say purified. Elution of the proteins fixed enables the resin to be re-used. This is particularly the case with clarification of beer and treatment of solutions containing haemoglobin with anionic resins.

Separation may be carried out discontinuously or continuously, with identical results.

In continuous operations, the resins allow easy filling of the column, a large output and easy elution.

The results obtained are virtually independent of the concentration of the solution treated, but are a function of the nature of the exchanging group in the resin, the pH, the ionic force and the flow rate of both the solutions to be treated and that used for elution.

The method of the invention may be applied to the food industries, particularly the dietetic, pharmaceutical and veterinary branches.

The following examples are given by way of illustration, but not by way of limitation of the invention:

EXAMPLE 1

Preparation of the ion exchange resin 100 g of silica with a particle size of 100 to 200 μm, a specific surface area of 24 m²/g, an average pore diameter of 1400 Å and a pore volume of 1 ml/g is dried at 150° C at reduced pressure for 5 hours.

The dried silica is placed in a solution of 250 ml of methylene chloride, 60 ml of distilled styrene, 20 ml of vinyltriethoxysilane and 0.5 g of azobis-isobutyronitrile.

The methylene chloride is evaporated at ambient temperature, then the impregnated silica is heated at 120° C and 3 bars for 6 hours to bring about cross-linking.

The silica is then suspended in 300 ml of xylene and heated at boiling point for 2 hours. When it has been filtered the silica is washed with acetone, then dried.

Analysis reveals a carbon content of 4% by weight relative to the coated silica.

50 g of the coated silica is suspended in 180 g of chloromethyl ether, containing 6 g of stannic chloride, then the mixture is heated under reflux for 4 hours in an anhydrous medium.

After cooling, the silica is drained and washed with 200 ml of a 50–50 mixture of dioxane and water containing 10 ml of hydrochloric acid. It is then washed with water until neutral and finally dried.

The carbon content is then 4.1% and the chlorine content 1.90%.

The product obtained is suspended in 150 ml of a 30% aqueous solution of trimethylamine and left in contact for 8 days at ambient temperature.

After draining and washing, an ion exchange resin is obtained, carrying

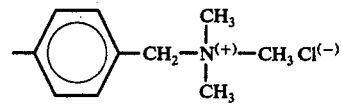

functional groups and with the following properties:

| | |
|---|---|
| carbon content | 4.8% |
| chlorine content | 2% |
| nitrogen content | 0.9% |
| quantity of polymer fixed | 3.3 mg/m² |
| exchange capacity | 0.5 meq/g. |

Treatment of an albumin solution 10 g of the ion exchange resin obtained is placed in a column 1 cm in diameter and kept compressed, then the resin is put into equilibrium at pH 6.5 with a 0.01 M phosphate buffer.

A 1% by weight albumin solution in the same buffer is percolated at 180 ml per hour until the column is saturated; this represents about 200 ml of solution. The resin is then washed with 100 ml of the same buffer.

The albumin fixed is then eluated by percolating an M solution of NaCl into the same buffer, at a flow rate of 180 ml per hour. 45 ml of solution enables the albumin to be recovered in a 3.3% by weight solution.

The ion exchange resin consequently has an albumin capacity of 150 mg per g and has enabled the albumin solution to be concentrated.

The same operation is repeated 30 times, and no swelling or aging of the ion exchange resin is observed.

EXAMPLE 2

Example 1 is repeated with a 0.2% instead of a 1% by weight solution of albumin.

The same results are obtained, that is to say the same concentration of albumin is obtained whatever the concentration of the solution treated.

EXAMPLE 3

Example 1 is repeated except that the protein is eluated with a 0.05 M, pH 6.5 citrate buffer. 59 ml of 2.5% by weight albumin solution is obtained.

This test shows the effect that the nature of the elution buffer has on the concentration of the solution obtained.

EXAMPLE 4

An albumin solution is treated in the same way as in Example 1 but using 41 g of the ion exchange resin in a column 1 cm in diameter and with an elution flow rate of 80 ml per hour instead of 180 ml per hour.

The concentration of the albumin solution obtained is 7% by weight. This shows that by increasing the working height of the column and reducing the elution speed, the concentration of the resultant solution can be increased.

EXAMPLE 5

Preparation of the resin 50 g of a silica, having a particle size of 40–100 μm, a specific surface area of 37 m$^2$/g, a pore diameter of 1100 Å and a pore volume of 1.05 ml/g, is placed in 150 ml of methylene chloride with 6.5 g of N,N-bis(2,3-epoxy propyl) ethylamine and 3 g of triethylenetetramine dissolved in it.

The methylene chloride is then evaporated at ambient temperature. The impregnated silica is heated at 60° C for 60 hours to bring about cross-linking. It is washed with boiling water and then with acetone.

The ionic exchange resin obtained is made up of silica coated with a cross-linked polymer containing

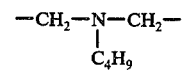

functional groups and has the following properties:

| carbon content | 8.8% |
| nitrogen content | 2.4% |
| quantity of polymer fixed | 3.3 mg/m$^2$ |
| exchange capacity | 1 meq/g |

Separation of γ-globulin 10 g of the ion exchange resin obtained is placed in a column 1 cm in diameter and kept compressed. The resin is put into equilibrium in 0.1 N hydrochloric acid, then in 0.02 N, pH 6.5 phosphate buffer.

20 ml of a 1% by weight solution of delipidized and lyophilized human serum in the same phosphate buffer is percolated at 100 ml per hour through the column.

The resin is then washed with 50 ml of the same phosphate buffer.

The solution emerging from the column contains the γ-globulin present in the initial solution, in an electrophoretically pure state.

The other proteins: α-globulins, β-globulins and albumin, also present in the initial solution, remain fixed on the resin. They are recovered by elution with a 3 N solution of NaCl in the same phosphate buffer.

If elution is effected by buffers of increasing ionic force, with an increase in the concentration of NaCl, solutions enriched with α-globulins, β-globulins and albumin are obtained.

EXAMPLE 6

Preparation of the resin

The procedure is the same as in Example 5, but the silica used has a particle size of 100 to 200 μm, and 6.5 g of N,N-bis (2,3-epoxy propyl) butylamine is used instead of 6.5 g of N,N-bis (2,3-epoxy propyl) ethylamine.

The ion exchange resin obtained consists of silica coated with a cross-linked polymer containing

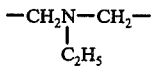

functional groups and has the following properties:

| carbon content | 9.2% |
| nitrogen content | 2.5% |
| quantity of polymer fixed | 3.2 mg/m$^2$ |
| exchange capacity | 1.1 meq/g |

Extraction of proteins 10 g of the ion exchange resin obtained is placed in a column 1 cm in diameter and kept compressed. The resin is successively put into equilibrium in 0.1 M hydrochloric acid, then in 0.01 N, pH 7.5 phosphate buffer.

30 ml of a 1% by weight solution of ultrafine-filtered milk serum powder, in the same phosphate buffer containing 75% by weight of proteins in percolated through the column at 80 ml per hour. The resin is then washed with 100 ml of the same phosphate buffer.

The solutions emerging from the column contain the fatty materials and lactose present in the initial solution.

The proteins, lactalbumins, lactoglobulins, serum albumin and a small part of the immunoglobulins, present in the initial solution, are fixed on the resin. The separated and purified proteins are recovered by elution with a 0.05 N, pH 4 Mac Ilvaine buffer.

EXAMPLE 7

Extraction of proteins 20 g of an ion exchange resin, similar to that in Example 1 but with a particle size from 200 to 500 μm, is placed in a column 2.5 cm in diameter and kept compressed.

The resin is succesively put into equilibrium in 0.1 N hydrochloric acid, then in 0.01 M, pH 7 tric HCl buffer.

600 ml of a solution consisting of 300 ml of the same tris-HCl buffer and 300 ml of delipidized milk serum, containing 0.5% by weight of soluble proteins, is percolated through the column at 300 ml per hour. The resin is then washed with 100 ml of the same buffer.

The solutions emerging from the column contain the lactose present in the initial solution.

The proteins: lactalbumins, lactoglobulins, serum albumin and a small part of the immunoglobulins, present in the initial solution, are fixed on the resin. They are eluated by passing a 0.1 N, pH 7 citrate-caustic soda buffer into the column. The solution obtained contains all the proteins fixed, at a concentration of 4% by weight.

The operation enables a mixture of pure proteins to be obtained, free from lactose and in a far more concentrated solution than the initial one.

No aging of the resin is observed after 30 successive operations.

EXAMPLE 8

Treatment of a pepsin solution 3 g of an ion exchange resin similar to that in Example 1 is placed in a column 1 cm in diameter.

The resin is washed with 100 ml of distilled water, then 150 ml of a solution of crude protein containing 20 pepsin units per ml is percolated through the column at 100 ml per hour. The resin is then washed with 20 ml of distilled water.

The solution emerging from the column and the washing water do not show any activity; the pepsin is fixed on the resin. The impurities have remained in the solution, as shown by dry extract determinations.

The pepsin fixed is then eluated by percolating an M solution of NaCl through it at 100 ml per hour.

16 ml of solution enable the pepsin to be recovered in a solution containing 170 pepsin units per ml.

The high concentration of the solution obtained is noted.

The resin is re-used after being washed with 50 ml of distilled water.

No aging of the resin is observed after 10 successive operations.

EXAMPLE 9

Preparation of the ion exchange resin 100g of silica, with a particle size of 100 to 200 μm, a specific surface area of 25 m$^2$/g, an average pore diameter of 1400 Å and a pore volume of 1.1 ml/g, is impregnated with a solution comprising 200 ml of methylene chloride, 24 g of acrylic acid, 6 g of diethylene glycol dimethacrylate and 0.4 g of benzoyl peroxide.

The methylene chloride is evaporated at ambient temperature and atmospheric pressure to constant weight; then the impregnated silica is heated at 80° C for 6 hours to bring about polymerization.

The silica is then suspended in 300 ml of water and heated at boiling point for 6 hour. When it has been filtered, the silica is washed with acetone, then dried under vacuum at 80° C.

The ion exchange resin obtained carries — COOH functional groups and has the following properties:

| | |
|---|---|
| carbon content | 10.55 % |
| quantity of polymer fixed | 7.2 mg/m$^2$ |
| exchange capacity | 1.05 meq/g. |

Treatment of a lysozyme solution 10 g of the ion exchange resin obtained is placed in a column 1 cm in diameter and kept compressed, then the resin is put into NH$_4^+$ form by percolating through the column 2 liters of a 0.5 M aqueous solution of ammonium acetate buffered at pH 8.2

The resin is then put into equilibrium at pH 6.5 with 100 ml of 0.02 N tris-maleic acid buffer.

A 1% by weight solution of lysozyme in the same buffer is percolated through the column at 180 ml per hour until the column is saturated; this represents about 200ml of solution. The resin is then washed with 100 ml of 0.02 N, pH 8.2 tris-maleic acid buffer.

The lysozyme fixed is then eluated by percolating an M solution of NaCl in the same buffer, at a flow rate of 180 ml per hour. 50 ml of solution enables the lysozyme to be recovered in a 2.5% by weight solution.

It follows that the ion exchange resin has a lysozyme capacity of 125 mg/g and that it enables the lysozyme solution to be concentrated.

EXAMPLE 10

Preparation of the exchange resin 100 g of silica, with a particle size of 100 to 200 μm, a specific surface area of 37 m$^2$/g, an average pore diameter of 1200 Å and a pore volume of 0.95 ml/g, is impregnated with a solution comprising 150 ml of methylene chloride, 60 ml of distilled styrene, 20 ml of vinyl-triethoxysilane and 0.5 g of azobis-isobutyronitrile.

The methylene chloride is evaporated at ambient temperature and atmospheric pressure to constant weight, then the impregnated silica is heated at 120° C for 6 hours to bring about cross-linking.

The silica is then suspended in 300 ml of xylene and heated at boiling point for 6 hours. When it has been drained the silica is washed with acetone and then dried at 80° C.

50 g of the modified silica obtained is suspended in 500 ml of chloroform, and 50 g of HSO$_3$Cl dissolved in 50 ml of chloroform is added dropwise. Hydrochloric acid is released. After the addition, the mixture is heated with agitation at 50° C for 4 hours.

When the product has been drained, washed with water until neutral, then washed with acetone and dried under vacuum at 80° C, an ion exchange resin is obtained, carrying —SO$_3$H functional groups and having the following properties:

| | |
|---|---|
| carbon content | 4% |
| sulphur content | 1.4% |
| quantity of polymer fixed | 2.8 mg/m$^2$ |
| exchange capacity | 0.43 meq/g. |

Extraction of haemoglobin 10 g of the ion exchange resin obtained is placed in a column 1 cm in diameter, then the resin is put into equilibrium at pH 6.5 with a 0.02 M phosphate buffer.

500 ml of a 0.2% by weight solution of haemoglobin in the same buffer is percolated through the column at 100 ml/h. The haemoglobin is adsorbed on the ion exchange resin. The colorless effluent solution no longer contains any haemoglobin and is thus purified.

The adsorbed haemoglobin is eluated by percolating a 0.5 M solution of ammonium carbonate, then the column is washed successively with 300 ml of 0.1 N caustic soda and 50 ml of 1N HCl, before being used again.

EXAMPLE 11

Treatment of milk serum 20 g of an ion exchange resin similar to that in Example 1 is placed in a first column 2.5 cm in diameter.

10 g of an ion exchange resin similar to that in Example 9 is placed in a second column 2.5 cm in diameter.

The two columns are arranged in series and the resins are washed with 500 ml of water.

500 ml of milk serum, adjusted to pH 7.5 by the addition of 0.1 N caustic soda, is filtered to eliminate insoluble materials, then percolated into column No. 1 and column No. 2 at 300 ml per hour.

The test in which proteins are precipitated by trichloroacetic acid shows that the milk serum emerging from column No. 2 no longer contains any protein.

The resins in both columns are washed by passing 100 ml of water through them.

The proteins: lactalbumins, lactoglobulins, serum albumin and a very small part of the immunoglobulins, present in the initial solution, are fixed on the resin in column No. 1. They are eluated as described in Example 7.

The proteins fixed on the resin in column No. 2 are essentially the immunoglobulins which were not fixed on the resin in column No. 1. They are eluated by percolating an M solution of ammonium carbonate through them. The solution obtained contains the immunoglobulins in a concentration of about 3% by weight. Immunoglobulins represent about 16% by weight of all the proteins in the initial solution.

The columns are then washed, by passing 500 ml of water through them, before being re-used.

No aging of the resins is observed after 10 successive operations.

EXAMPLE 12

Treatment of proteins from beer 60 g of an ion exchange resin similar to that in Example 9 is placed in a column 2.5 cm in diameter, then washed with 250 ml of water.

5 liters of non-clarified beer is percolated through at 100 ml per hour. The beer emerging from the column is no longer precipitated by the addition of picric acid and has the properties of a clarified beer.

The products fixed on resin are essentially proteins. They are eluated by percolating 400 ml of N/10 hydrochloric acid.

The resin is washed, by passing 250 ml of water through it, before being re-used.

We claim:

1. A method of separating proteins from solution, comprising putting a solution of proteins into contact with an ion exchange resin, comprising a porous inorganic carrier with a particle size from 4 μm to 5 mm, a specific surface area of approximately 5 to 150 m²/g, a pore diameter of 500 to 2500 Å and a pore volume of 0.4 to 2 ml/g, coated with less than 15 mg/m² of a film of cross-linked polymer, containing or carrying either tertiary amines or quaternary ammonium salts, as anion exchanging groups, or acid functions as cationic exchanging groups, wherein at least one protein becoming fixed onto the ion exchange resin, and eluting the fixed protein(s) from the ion exchange resin.

2. The method of claim 1, in which the inorganic carrier is selected from the group consisting of metallic oxide, titanium oxide, aluminas, and silicas.

3. The method of claim 1, in which the anion-exchanging groups are represented by formulae selected from the group consisting of

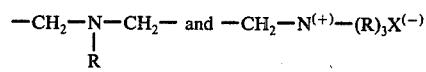

in which R, which may be identical or different, represents a group selected from the group consisting of an alkyl and hydroxyalkyl group having 1 to 4 carbon atoms and X represents an inorganic or organic ion.

4. The method of claim 1, in which the cation-exchanging groups are selected from the group consisting of carboxylic, sulphonic and phosphonic acid functions.

5. The method of claim 1, in which the cross-linked polymer is derived from monomers selected from the group consisting of (a) epoxy compounds cross-linked with polyamines as catalyst, (b) formaldehyde cross-linked by polycondensation with monomers selected from the group consisting of urea, melamine, polyamines and phenols, (c) vinyl monomers selected from the group consisting of vinyl pyridine, styrene and derivatives thereof, vinylbenzoic acid, acrylic acid and methacrylic acid cross-linked with polyfunctional monomers selected from the group consisting of mono- or polyalkyleneglycol diacrylate or dimethacrylate, divinylbenzene, vinyltrialkoxysilane, vinyltrihalogenosilane and bis methylene acrylamide.

6. The method of claim 1, in which the proteins are selected from the group consisting of albumin, lactalbumins, egg albumin, serum albumin, haemoglobin, α, β and γ-globulins, lactoglobulins, fibrinogen, urease, trypsin, lysozyme, pepsin, proteases and cytochrome.

7. The method of claim 1, in which the protein solutions to be treated are selected from the group consisting of milk serum, beer, blood, extracts from organs and industrial effluents.

8. The method of claim 1, in which the required protein remains in the solution, and the other proteins in the solution are fixed on the ion exchange resin.

9. The method of claim 1, in which all the proteins are fixed and the solution purified.

10. The method as claimed in claim 1 in which the exchanger has an exchange capacity of less than 2 meg./g.

* * * * *

UNITED STATES PATENT OFFICE
CERTIFICATE OF CORRECTION

Patent No. 4,100,149　　　　　　　Dated July 11, 1978

Inventor(s) Francois Meiller and Bernard Mirabel

It is certified that error appears in the above-identified patent and that said Letters Patent are hereby corrected as shown below:

Column 7, line 22, after "crude", correct "protein" to -- pepsin -- .

Signed and Sealed this

Twentieth Day of March 1979

[SEAL]

Attest:

RUTH C. MASON
Attesting Officer

DONALD W. BANNER
Commissioner of Patents and Trademarks